United States Patent
Bin Md. Noor et al.

(10) Patent No.: US 9,428,440 B2
(45) Date of Patent: Aug. 30, 2016

(54) PROCESS FOR REFINING GLYCERIDE OIL AND PURIFYING TRIGLYCERIDE OIL OBTAINED BY SUCH PROCESS

(75) Inventors: Ahmadilfitri Bin Md. Noor, Selangor Darul Ehsan (MY); Mohd. Suria Affandi Yusoff, Selangor Darul Ehsan (MY); Khairudin Hashim, Selangor Darul Ehsan (MY)

(73) Assignee: SIME DARBY MALAYSIA BERHAD, Kuala Lumpur (MY)

( * ) Notice: Subject to any disclaimer, the term of this patent is extended or adjusted under 35 U.S.C. 154(b) by 0 days.

(21) Appl. No.: 14/376,373

(22) PCT Filed: Aug. 28, 2012

(86) PCT No.: PCT/MY2012/000240
§ 371 (c)(1),
(2), (4) Date: Aug. 1, 2014

(87) PCT Pub. No.: WO2013/115634
PCT Pub. Date: Aug. 8, 2013

(65) Prior Publication Data
US 2014/0357888 A1 Dec. 4, 2014

(30) Foreign Application Priority Data
Feb. 2, 2012 (MY) .................. PI 2012000467

(51) Int. Cl.
| | |
|---|---|
| C07C 67/48 | (2006.01) |
| C07C 67/58 | (2006.01) |
| A23D 9/04 | (2006.01) |
| B01D 15/34 | (2006.01) |
| C11B 3/10 | (2006.01) |
| C07C 69/604 | (2006.01) |
| B01J 20/283 | (2006.01) |
| B01J 20/285 | (2006.01) |
| B01J 20/28 | (2006.01) |

(52) U.S. Cl.
CPC .............. *C07C 67/58* (2013.01); *A23D 9/04* (2013.01); *B01D 15/34* (2013.01); *B01J 20/283* (2013.01); *B01J 20/28004* (2013.01); *B01J 20/285* (2013.01); *B01J 20/28057* (2013.01); *B01J 20/28083* (2013.01); *C07C 69/604* (2013.01); *C11B 3/10* (2013.01)

(58) Field of Classification Search
CPC ........ A23D 9/04; B01D 15/34; C07C 67/58; C07C 69/604; B01J 20/28004; B01J 20/28057; B01J 20/28083; B01J 20/283; B01J 20/285; C11B 3/10
See application file for complete search history.

(56) References Cited

U.S. PATENT DOCUMENTS

| 2010/0210861 A1 | 8/2010 | Woods et al. |
| 2011/0262592 A1 | 10/2011 | Kang et al. |

FOREIGN PATENT DOCUMENTS

| EP | 0059997 | * | 2/1982 |
| EP | 0059997 | * | 9/1982 |

OTHER PUBLICATIONS

Dubé, Marc A. et al. "A Comparison of Attenuated Total Reflectance-FTIR Spectroscopy and GPC for Monitoring Biodiesel Production", Journal of the American Oil Chemists' Society, vol. 81, No. 6, Jun. 1, 2008, pp. 599-603.
Caldwell, J. D. et al. "High Performance Liquid Chromatography-Size Exclusion Chromatography for Rapid Analysis of Total Polar Compounds in Used Frying Oils", Journal of the American Oil Chemists' Society, vol. 88, No. 11, May 7, 2011, pp. 1669-1674.
Christopoulou, Constantina N. et al. "High Performance Size Exclusion Chromatography of Fatty Acids, Mono-, Di- and Triglyceride Mixtures", Journal of the American Oil Chemists' Society, vol. 63, No. 5, May 1, 1986, pp. 679-684.
European Patent Office. International Search Report dated Apr. 4, 2013. International PCT Application No. PCT/MY2012/000240. 3 pages.

* cited by examiner

*Primary Examiner* — Yevegeny Valenrod
*Assistant Examiner* — Blaine G Doletski
(74) *Attorney, Agent, or Firm* — Moore & Van Allen PLLC; Henry B. Ward, III

(57) ABSTRACT

The present invention relates to a process for refining glyceride oil by size exclusion chromatography to obtain a triglyceride enriched fraction. The process comprises passing a glyceride oil through a size exclusion column packed with porous particles having a mass weighted mean particle size of 20 to 1,000 µm and an average pore size of 10 to 150 Å without using any solvent and collecting an eluate fraction enriched in triglyceride. The process may further comprise passing a solvent through the size exclusion column after the eluate fraction enriched in triglyceride is collected to obtain a partial glyceride enriched fraction. The process can suitably be used to produce triglyceride enriched fraction having a triglyceride content that is close to 100%.

16 Claims, No Drawings

PROCESS FOR REFINING GLYCERIDE OIL AND PURIFYING TRIGLYCERIDE OIL OBTAINED BY SUCH PROCESS

FIELD OF THE INVENTION

The present invention relates to a process for refining a glyceride oil. More particularly, the invention relates to a process for refining a glyceride oil using size exclusion chromatography to obtain a triglyceride enriched fraction. The invention also provides a triglyceride oil obtained by the process.

BACKGROUND OF THE INVENTION

Vegetable oils that are produced by industrial extraction processes are normally subjected to a number of refining steps in order to render them palatable, to remove extraction solvents and/or to improve storage stability. Notable exceptions are cold pressed oils such as extra virgin olive oil.

The most common types of industrially produced vegetable oils are fruit oils (e.g. palm oil) and seed oils (e.g. sunflower oil).

Crude palm oil produced using known methods in the prior art usually contains substantial amounts of components, such as free fatty acids, phospholipids and malodorous substances. These substances usually need to be removed in order to render the oil palatable and stable while in storage.

Oil seeds like linseeds are usually milled for a long time to produce oil and meal. The current methods employed in producing the crude quality seed oils usually contain appreciable quantities of components that need to be removed. Besides the undesired components that need to be removed, solvent residue also needs to be removed from these seed oils to render the seed oils suitable for consumption.

A sequence of oil refining steps is commonly used to produce a fully refined or refined, bleached and deodorised (RBD) oil. These oil refining steps include (i) removing gums (mainly phospholipids) from the oil; (ii) removing free fatty acids; (iii) removing absorbable compounds (this step is commonly referred to as "bleaching," but it does more than just decrease the absorbance of the oil); and (iv) removing malodorous compounds contain in the oil.

The main component of vegetable oils, animal fats, marine oils and milk fat are glycerides, i.e. esters formed from glycerol and fatty acids. Triglycerides usually represent the bulk of the glycerides contained in these oils and fats. Mono- and diglycerides are usually present in minor quantities. Glycerophospholipids are usually present in higher quantity and they are usually removed in the degumming step in an oil refining process.

The presence of monoglycerides and diglycerides in commercially available refined oils and fats has several disadvantages. One such disadvantage is that the presence of diglycerides will affect the crystallization and melting behaviour of the triglyceride present in these oils and fats (Siew, W L, "Understanding the Interactions of Diacylglycerols with Oils for Better Product Performance", Palm Oil Developments, 2001: 36, 6-11).

There are methods known to remove monoglycerides and diglycerides from the refined oils and fats. One such method is to remove them by converting them into triglycerides. U.S. Pat. No. 5,061,498 describes a method of converting partial glycerides (including monoglycerides, diglycerides, glycerophospholipids) within the fats and oils to triglycerides. The method comprises the steps of treating the fats and oils with at least two lipases which are different in fatty acid specificity and/or position specificity, with the lipase having different fatty acid specificity being selected from the group consisting of lipases acting on short chained fatty acids, lipases acting on middle chained fatty acids, lipases acting on all fatty acids and lipases acting on unsaturated fatty acids. The said lipase having different position specificity is selected from the group consisting of lipases having no position specificity and lipases having 1,3-position specificity. The method described in this publication is laborious and cannot be used to produce oils containing triglyceride in an amount of close to 100%.

Consequently, there is a need for a refining process that effectively removes monoglycerides and diglycerides from glyceride oil so as to enable cost-effective production of a refined triglyceride oil of high purity.

SUMMARY OF THE INVENTION

The above and other problems are solved and an advance in the art is made by a process for refining glyceride oil using size exclusion chromatography in accordance with this invention. It is an advantage of a process in accordance with this invention that a process for refining glyceride oil is provided to enable production of a refined triglyceride oil of high purity by effectively removing the undesired components from the glyceride oil. A second advantage of this invention is that the process enables a triglyceride oil of high purity to be obtained without the use of any solvent. A third advantage of this invention is that the process can be used to produce partial glyceride enriched fraction containing relatively high amounts of diglycerides, monoglycerides and/or glycerophospholipids.

In an embodiment of this invention, a process for refining a glyceride oil to obtain a fraction enriched in triglyceride is provided. The process comprises the steps of passing a glyceride oil through a size exclusion column packed with porous particles having a mass weighted mean particle size of 20 to 1,000 μm and an average pore size of 10 to 150 Å without using any solvent and collecting an eluate fraction enriched in triglyceride. The process may advantageously be used to refine glyceride oil that contains 80 wt % to 99.8 wt % of triglyceride and 1 wt % to 20 wt % of partial glyceride selected from monoglycerides, diglycerides, glycerophospholipids and combinations thereof.

In the embodiment of this invention, the fraction enriched in triglyceride contains at least 98 wt % of triglyceride and less than 2 wt % of the partial glyceride.

In some embodiments of this invention, the process further comprises passing a solvent through the size exclusion column after the eluate fraction enriched in triglyceride is collected to obtain a solvent extract containing a partial glyceride enriched fraction, and isolating the partial glyceride enriched fraction from the solvent extract. In some of these embodiments, the solvent used in these steps include acetone, $C_5$-$C_8$ alkanes or combinations thereof.

In some embodiments of this invention, at least 80 wt % of the porous particles having a diameter in the range of 60 to 800 μm.

In another embodiment of this invention, a triglyceride oil obtained as the fraction enriched in triglyceride in the process according to this invention is provided. In some embodiments of this invention, the triglyceride oil comprising at least 99.5 wt % of triglyceride and less than 0.3 wt % of diglyceride. The triglyceride oil may further comprise not more than 1.0 wt % of glyceride esters of fatty acids having a molecular weight of 640 g or less.

DETAILED DESCRIPTION OF THE INVENTION

Size-exclusion chromatography (SEC) is a chromatographic method in which molecules are separated by their size. It is usually applied to large molecules or macromolecular complexes. Typically, when an aqueous solution is used to transport the sample through the column, the technique is known as gel-filtration chromatography, versus the name gel permeation chromatography, which is used when an organic solvent is used as a mobile phase. SEC is widely used in polymer characterization method because of its ability to provide good molar mass distribution (Mw) results for polymers.

The main application of gel-filtration chromatography is the fractionation of proteins and other water-soluble polymers, while gel permeation chromatography is used to analyze the molecular weight distribution of organic-soluble polymers.

The inventors have unexpectedly discovered that SEC can be used to refine glyceride oil to obtain a triglyceride enriched fraction. This is done by fractionating the glyceride oil into a triglyceride enriched fraction and a partial glyceride enriched fraction. The chromatographic separation of triglyceride and partial glyceride in the process of the invention results from the fact that partial glyceride elutes more slowly from the column than triglyceride. The difference in elution time is believed to be based on a difference in volume that the glyceride molecules have access to, when they travel through the column. The smaller partial glyceride can penetrate the pore system of the stationary phase more effectively than the triglyceride. Consequently, the partial glyceride has access to not only the interparticle volume but also to a substantial fraction of the pore volume. In contrast, the triglyceride has access to little more than just the interparticle volume. Thus, triglyceride and partial glyceride will elute through the porous stationary phase at different rates. The elution time of the triglyceride is determined mainly by the interparticle volume, and the elution time of the partial glyceride is determined by the interparticle volume and the fraction of the pore volume that is accessible to the partial glyceride.

It is noted that size exclusion may not be the only mechanism that is responsible for the successful separation of the glyceride oil into triglyceride and partial glyceride in the process of the invention. The non-covalent interactions between the stationary phase (for example, the porous particles) and for example, the partial glyceride may also play a role in the separation.

In accordance with an embodiment of the invention, there is provided a process for separating glyceride oil into a triglyceride enriched fraction and a partial glyceride enriched fraction using size exclusion chromatography. The process comprises the steps of passing the glyceride oil through a size exclusion column packed with porous particles having a mass weighted mean particle size of preferably 20 to 1,000 μm and with an average pore size of 10 to 150 Å, and collecting an eluate fraction enriched in triglyceride.

The term "oil" as used herein refers to a lipid material that may be liquid or solid at ambient temperature (20° C.).

The term "glyceride" as used-herein refers to esters formed from at least glycerol, one or more fatty acids and optionally another acid, e.g. phosphoric acid.

The term "triglyceride enriched fraction" or "fraction enriched in triglyceride" as used herein refers to triglyceride that has a significantly higher triglyceride content (calculate by weight of total glycerides) than the glyceride oil that is used as the starting material in the process of the invention.

The term "partial glyceride enriched fraction" as used herein refers to a partial glyceride having a partial glyceride content (calculated by weight of total glycerides) that is significantly higher (for example, at least 50% higher) than that of the glyceride oil that is used as the starting material in the process of the invention. The partial glyceride preferably is selected from monoglyceride, diglyceride, glycerophospholipid and combinations thereof.

The term "porous particles" as used herein refers to particles that contain channels, pores or cavities that provide access to the oil and any solvent that may be used.

The term "pore volume" as used herein refers to the total volume contribution of all pores excluding the volume contribution of closed pores.

As explained hereinabove, triglyceride elutes faster from the column employed in the process of the present invention than partial glyceride as the triglyceride has less access to the pore volume. Consequently, the triglyceride enriched fraction is removed as the first eluate in one embodiment of the present invention.

SEC procedures described in the prior art typically employ a solvent to separate components dissolved with that solvent. In the process of the present invention, the glyceride oil can be separated without using any organic or aqueous solvent as eluent. The pore size of the porous particles used in the size exclusion column allows the smaller molecules (for example, the partial glycerides) to be trapped in the pores of the porous particles and the bigger molecules (for example, the triglycerides) to pass through the porous particles as an eluent. In this case, the mobile phase employed in the process preferably consists predominantly of the glyceride oil.

The glyceride oil that is subjected to the SEC process preferably contains less than 1.0 wt % of water, more preferably less than 0.5 wt %, and most preferably less than 0.2 wt % of water.

The porous particles employed in the column preferably have a relatively uniform diameter. Preferably, at least 80 wt % of the porous particles have a diameter in the range of 60 to 800 microns (μm), more preferably in the range of 100 to 600 μm, and most preferably in the range of 200 to 500 μm. The porous particles may be made of various materials. Preferably, the porous particles are porous silica particles, porous cross-linked polystyrene particles or combinations thereof. Most preferably, the porous particles are porous silica particles.

The specific surface area of the porous particles is a measure of the porosity of the particles. Preferably, the porous particles have a specific surface area in the range of 200 to 1,200 $m^2/g$, more preferably in the range of 300 to 1,000 $m^2/g$, even more preferably in the range of 400 to 800 $m^2/g$, and most preferably in the range of 420 to 600 $m^2/g$.

The pore size of the porous particles is believed to be very relevant to the separation efficiency of the present process. The smaller the pore size, the better will be the separation of the components of the oil. A large pore size, in contrast, is generally considered to produce poorer separation results. In a preferred embodiment, the pore size of the porous particles is in the range of 10 to 150 Angstroms (Å), preferably 20 to 120 Å, more preferably 30 to 100 Å, even more preferably 35 to 90 Å, and most preferably in the range of 40 to 80 Å.

The pore volume of the porous particles typically lies in the range of 0.4 to 1.2 ml/g. Preferably, the pore volume lies in the range of 0.5 to 1.1 ml/g, more preferably in the range of 0.6 to 1.0 ml/g, and most preferably in the range of 0.7 to 0.9 ml/g.

The chromatographic separation of the glyceride oil in the process of the present invention is preferably performed at a temperature in the range of 10 to 70° C., more preferably at a temperature of 15 to 65° C., and most preferably at a temperature of 30 to 60° C.

The process of the present invention may be applied to RBD oils, as well as to crude oils, including oils that have not been subjected to de-gumming. Preferably, however, the process is employed to fractionate de-gummed oils. When the process is employed to fractionate de-gummed oils, the glyceride oil used in the process preferably has a phosphorus content of not more than 10 mg/kg, and more preferably, not more than 5 mg/kg.

Examples of glyceride oil that can be fractionated by the process of the invention include vegetable oils, animal fats, marine oils (e.g. fish oil) and milk fats, fractions of these glyceride oils and mixtures of the oils and/or fractions. Preferably, the glyceride oil that is used as the starting material in the process is selected from non-hydrogenated vegetable oil, a fraction of such oil or a combination of two or more of these oils. More preferably, the vegetable oil is selected from palm oil, palm kernel oil, coconut oil, sunflower oil, soybean oil, rapeseed oil, linseed oil, olive oil and combinations thereof. Most preferably, the vegetable oil is palm oil or a fraction thereof, including but is not limited to an olein fraction or a stearin fraction.

The benefits of the process of the present invention are particularly pronounced in that the process is employed to fractionate glyceride oil containing very high amount of triglyceride and relatively low amount of partial glyceride. In one embodiment of the present invention, the glyceride oil used in the process contains 80 to 99.8 wt % of triglyceride and 1 to 20 wt % of partial glyceride. Preferably, the glyceride oil contains 90 to 99.8 wt % of triglyceride, 0.2 to 7.0 wt % of diglyceride, 0 to 3 wt % of monoglyceride and 0 to 4 wt % of glycerophospholipid. More preferably, the glyceride oil contains 94.0 to 99.8 wt % of triglyceride, 0.2 to 5.0 wt % of diglyceride, 0 to 2 wt % of monoglyceride and 0 to 1 wt % of glycerophospholipid.

The benefits of the process of the present invention become particularly manifest when the process is employed for industrial scale fractionation of glyceride oil. The process can easily be controlled by controlling the flow rate of the oil, the temperature of the process, the pressure within the size exclusion column, etc. This provides for a more predictable process that is suitable for industrial use. In the process of the present invention, the glyceride oil can be processed at a rate of at least 50 kg per hour.

The process in accordance with this invention offers an advantage that it can produce a triglyceride enriched fraction in the form of very pure triglyceride oil. The triglyceride enriched fraction obtained by the process preferably contains at least 98 wt % of triglyceride and less than 2 wt % of the partial glyceride, more preferably at least 98.5 wt % of triglyceride and less than 1.5 wt % of the partial glyceride. Most preferably, the triglyceride enriched fraction contains at least 99.0 wt % of triglyceride and less than 1.0 wt % of the partial glyceride.

The triglyceride enriched fraction preferably contains at least 50% less partial glyceride than the partial glyceride present in the glyceride oil that is employed as the starting material. More preferably, the triglyceride enriched fraction contains at least 70% less partial glyceride, and most preferably at least 90% less partial glyceride than the partial glyceride present in the glyceride oil that is employed as the starting material.

In one embodiment of the present invention, the triglyceride enriched fraction is collected as an eluate from the size exclusion column at least until the glyceride oil contained within the column has an average partial glyceride content of at least 5 to 10 wt %, depending on the type of glyceride oil that is used as the starting material. In one embodiment, the column can have an average partial glyceride content of at least 5 wt %. In other embodiments, the column can have an average partial glyceride content of at least 7 wt % or at least 10 wt %.

Another advantage of the process of the present invention is that the process can be used to produce a partial glyceride enriched fraction containing relatively high amounts of diglycerides, monoglycerides and/or glycerophospholipids. The partial glyceride enriched fraction can be obtained by removing the partial glyceride from the size exclusion column after the triglyceride enriched fraction is collected as an eluate from the column. In one embodiment of this invention, the partial glyceride enriched fraction is removed from the column by using an organic solvent. This is done by contacting the porous particles within the column with an organic solvent and collecting a solvent extract containing the partial glyceride enriched fraction after the solvent passed through the column. This is followed by isolating the partial glyceride enriched fraction from the solvent extract so obtained. The partial glyceride enriched fraction can be isolated from the solvent extract by any suitable methods known to those skilled in the art. The method may include, but is not limited to, treating the solvent extract with heat, for example, by distillation or distillation under reflux conditions.

The organic solvent that can be used to elute the partial glyceride in the manner described hereinabove preferably is selected from, but not limited to, acetone, $C_5$-$C_8$ alkanes and combinations thereof. More preferably, the organic solvent is selected from acetone, hexane and combinations thereof. Most preferably, the organic solvent is hexane.

The partial glyceride enriched faction may contain monoglyceride, diglyceride, glycerophospholipids or a combination thereof. It should be noted that the partial glyceride enriched fraction may be collected as separate fraction upon elution with a suitable solvent. Thus, it is possible to obtain, for instance, a fraction that is highly enriched in diglyceride, a fraction that is highly enriched in monoglyceride and/or a fraction that is highly enriched in glycerophospholipid.

In another embodiment of the invention, a triglyceride oil obtained by the process as described hereinabove is provided.

The triglyceride oil obtained by the process of the present invention has a unique 'fingerprint' as the SEC treatment effectively removes a number of the components that are typically present in the glyceride oil, notably diglyceride and monoglyceride. Typically, the triglyceride oil comprises at least 99.5 wt % of triglcyeride and less than 0.3 wt % of diglyceride, more preferably, the triglyceride oil contains at least 99.7 wt % of triglyceride and less than 0.3 wt % of diglyceride, and most preferably, the triglyceride oil contains at least 99.9 wt % of triglyceride and less than 0.1 wt % of diglyceride.

The amount of monoglyceride present in the triglyceride oil obtained by the process of the invention typically does not exceed 0.5 wt %, more preferably, the amount of monoglyceride does not exceed 0.1 wt %.

The triglyceride oil of the present invention typically has a fatty acid distribution that is typical of a naturally occurring oil or a fraction thereof, or of mixtures of such oils and/or fractions. Preferably, at least 80 wt % of the fatty acid residues present in the triglyceride oil are $C_{12}$-$C_{20}$ fatty acids. According to a particular preferred embodiment of the present invention, at least 80 wt % of the fatty acid residues present in the triglyceride oil are $C_{16}$-$C_{18}$ fatty acids.

The triglyceride oil is preferably selected from a vegetable oil, a vegetable oil fraction, a mixture of vegetable oils, a mixture of vegetable oil fractions and a mixture of one or more vegetable oils and one or more vegetable oil fractions, depending on the type of starting material used in the process. Preferably, the vegetable oils are selected from palm oil, palm kernel oil, coconut oil, sunflower oil, soybean oil, rapeseed oil, linseed oil, olive oil and combinations thereof. Most preferably, the vegetable oil is palm oil.

The triglyceride oil of the present invention is special in that it contains not more than a very limited amount of glyceride fatty acid esters (including triglyceride as well as partial glyceride) having a molecular weight of 612 g or less. In a preferred embodiment, the triglyceride oil contains not more than 1.0 wt % of glyceride esters of fatty acids having a molecular weight of 612 g or less, more preferably, the triglyceride oil contains not more than 0.5 wt % and most preferably, not more than 0.2 wt % of glyceride esters of fatty acids having a molecular weight of 612 g or less.

In another preferred embodiment, the triglyceride oil contains not more than 1.0 wt % of glyceride esters of fatty acids having a molecular weight of 640 g or less. More preferably, the triglyceride oil contains not more than 0.5 wt % and most preferably, not more than 0.2 wt % of glyceride esters of fatty acids having a molecular weight of 640 g or less.

The following examples are provided to further illustrate and describe particular specific embodiments of the present invention, and are in no way to be construed to limit the invention to the specific procedures, conditions or compositions described therein.

EXAMPLES

Example 1

A column with an internal diameter of 6 cm and a length of 20 cm was filled with 200 g of silica gel particles (ZEOprep 60, ZeochemAG) having a diameter of 200 to 500 μm. The column was surrounded by a heating mantle that was set to keep the column temperature at 70° C.

Next, 1,500 ml of RBD palm oil that had been preheated to 70° C. was passed over the column at a gravity flow. Six consecutive fractions of eluate of each 200 g were collected and analysed. The results are shown in Table 1 (DG=diglyceride, TG=triglyceride).

TABLE 1

| | Starting material | \\multicolumn{6}{c}{Fractions (wt %)} | | | | | |
| --- | --- | --- | --- | --- | --- | --- | --- |
| | | $1^{st}$ | $2^{nd}$ | $3^{rd}$ | $4^{th}$ | $5^{th}$ | $6^{th}$ |
| FFA (%) | | 0.011 | 0.009 | 0.011 | 0.024 | 0.036 | 0.043 |
| DG C34 | 0.47 | 0 | 0 | 0 | 0.25 | 0.36 | 0.38 |
| DG C36 | 1.85 | 0 | 0 | 0 | 1.44 | 1.77 | 1.84 |
| DG C38 | 0.88 | 0 | 0 | 0 | 0.85 | 1 | 1.02 |
| TG C46 | 0.72 | 0.74 | 0.81 | 0.83 | 0.77 | 0.75 | 0.73 |
| TG C48 | 8.53 | 7.43 | 8.28 | 8.33 | 7.74 | 7.78 | 7.65 |
| TG C50 | 37.99 | 37.82 | 38.91 | 38.94 | 38.06 | 37.64 | 37.74 |
| TG C52 | 38.81 | 41.77 | 40.7 | 40.58 | 39.7 | 39.52 | 39.46 |
| TG C54 | 10.28 | 11.67 | 10.8 | 10.83 | 10.67 | 10.68 | 10.67 |
| TG C56 | 0.45 | 0.57 | 0.5 | 0.49 | 0.52 | 0.51 | 0.53 |

At the end of the experiment, the silica gel was collected and the oil inside was extracted from the top, middle and bottom of the packed column. The results are shown in Table 2.

TABLE 2

| | Top | Centre | Bottom |
| --- | --- | --- | --- |
| DG - C34 | 0.3 | 0.25 | 0.27 |
| DG - C36 | 1.52 | 1.33 | 1.3 |
| DG - C38 | 0.88 | 0.78 | 0.76 |
| TG - C46 | 0.85 | 0.91 | 0.84 |
| TG - C48 | 8.26 | 8.11 | 8.27 |
| TG - C50 | 38.48 | 38.26 | 38.14 |
| TG - C52 | 38.98 | 39.43 | 39.39 |
| TG - C54 | 10.18 | 10.44 | 10.54 |
| TG - C56 | 0.48 | 0.48 | 0.5 |

The results in Table 1 shows that the process of the invention can produce an oil with high triglyceride content (TG) after passing the starting material through a size exclusion column. We can see that the triglyceride content in the oil reduces as the oil travels down the column as more and more partial glycerides (DG) are trapped in the silica gel particles. When the partial glycerides reach a saturation point, they will start to appear in the eluant.

Table 2 shows that the concentration of the partial glycerides in the column is almost the same at the top, middle and bottom of the column.

Example 2

Two columns identical to the one described in Example 1 were filled with two different types of silica gel particles:

SG01: diameter 200 to 500 μm (ZEOprep 60, Zeochem AG)

SG02: diameter 60 to 200 μm (ZEOprep 60, Zeochem AG)

Again, the columns were kept at 70° C. Next, 500 g of RBD palm oil that had been preheated to 70° C. was passed over each of the two columns at a gravity flow. For each column, the first 100 g of eluate was collected and analysed. The results are shown in Table 3.

TABLE 3

| | Starting Material (wt %) | SG01 (wt %) | SG02 (wt %) |
| --- | --- | --- | --- |
| Melting point (° C.) | 37.5 | 37.2 | 34.6 |
| SFC (%) 0° C. | 67.19 | 74.07 | 73.94 |

TABLE 3-continued

|  | Starting Material (wt %) | SG01 (wt %) | SG02 (wt %) |
|---|---|---|---|
| 10° C. | 52.52 | 60.07 | 60.22 |
| 20° C. | 24.02 | 27.53 | 25.97 |
| 30° C. | 7.4 | 8.35 | 6.87 |
| 35° C. | 4.09 | 4.38 | 3.23 |
| 40° C. | 0.3 | 0.89 | 0.04 |
| DG -C34 | 0.32 | 0 | 0 |
| DG -C36 | 1.41 | 0 | 0 |
| DG -C38 | 0.78 | 0 | 0 |
| TG - C46 | 0.68 | 0.56 | 0.34 |
| TG - C48 | 7.71 | 7.01 | 4.68 |
| TG - C50 | 38.4 | 38.12 | 35.08 |
| TG - C52 | 39.3 | 41.76 | 44.6 |
| TG - C54 | 10.18 | 11.25 | 13.97 |
| TG - C56 | 0.42 | 0.49 | 0.78 |

The results in Table 3 show that the process of the invention can be carried with porous particles having a diameter in the range of 60 to 500 µm.

Example 3

A column with an internal diameter of 6 cm and a length of 20 cm was filled with 200 g of silica gel particles (ZEOprep 60, Zeochem AG) having a diameter of 200 to 500 µm. The column was surrounded by a heating mantle that was set to keep the column temperature at 70° C.

Next, 500 g of RBD palm oil that had been preheated to 70° C. was passed over the column at a gravity flow and 300 g of eluate was collected and analysed. The starting material, i.e. the RBD palm oil and a high grade refined palm oil (Jomalina Guaranteed Quality Palm Oil (JGQPO) produced by Sime Darby, Jomalina, Malaysia) were also analysed in the same manner. The results are shown in Table 4.

TABLE 4

|  |  | Starting Material (wt %) | High-grade Refined palm oil (wt %) | Eluate (wt %) |
|---|---|---|---|---|
| Iodine Value |  | 52.78 | 53.42 | 51.98 |
| Peroxide Value |  | 2.99 | 0 | 2.76 |
| FFA |  | 0.03 | 0.02 | 0.01 |
| Melting point (° C.) |  | 39.00 | 35.90 | 38.40 |
| Colour |  | 3R 50Y | 1.3R 10Y | 1R 10Y |
| Smoke Point (° C.) |  | 226 | 220 | 220 |
| Rancimat (H) |  | 14.07 | 14.40 | 15.04 |
| SFC (° C.) | 0° C. | 67.641 | 70.458 | 74.614 |
|  | 5° C. | 65.899 | 67.877 | 72.636 |
|  | 10° C. | 56.102 | 56.928 | 62.898 |
|  | 15° C. | 44.628 | 43.107 | 48.384 |
|  | 20° C. | 30.29 | 27.811 | 32.415 |
|  | 25° C. | 17.733 | 15.732 | 19.274 |
|  | 30° C. | 10.234 | 8.42 | 10.009 |
|  | 35° C. | 5.183 | 3.92 | 5.117 |
|  | 40° C. | 1.308 | 0.422 | 2.757 |
|  | 45° C. | 0.309 | −0.247 | 0.152 |
| Fatty acids (%) | C12 | 0.17 | 0.16 | 0.13 |
|  | C14 | 1.03 | 0.97 | 1.02 |
|  | C16 | 44.19 | 43.07 | 44.23 |
|  | C16:1 | 0.17 | 0.16 | 0.2 |
|  | C18 | 4.20 | 4.18 | 4.32 |
|  | C18:1 | 39.99 | 40.65 | 39.98 |
|  | C18:2 | 9.73 | 10.30 | 9.58 |
|  | C20 | 0.34 | 0.34 | 0.35 |
|  | C18:3 | 0.19 | 0.18 | 0.19 |
| TG (%) | C34 | 0.46 | 0.34 | 0.00 |
|  | C36 | 1.78 | 1.71 | 0.00 |
|  | C38 | 0.95 | 1.05 | 0.00 |
|  | C46 | 0.79 | 0.70 | 0.77 |
|  | C48 | 8.08 | 7.27 | 8.00 |

TABLE 4-continued

|  | Starting Material (wt %) | High-grade Refined palm oil (wt %) | Eluate (wt %) |
|---|---|---|---|
| C50 | 37.32 | 36.85 | 38.53 |
| C52 | 38.89 | 39.96 | 40.57 |
| C54 | 11.04 | 11.41 | 11.43 |
| C56 | 0.70 | 0.70 | 0.69 |
| Sum TG C46-56 | 96.82 | 96.89 | 99.99 |

The results in Table 4 show that the triglyceride oil obtained by the process of the invention has a quality that is comparable to or if not, better than the starting material (RBD palm oil) and the high grade refined palm oil (JGQPO).

Storage stability of the aforementioned oils was assessed by storing the oils for 9 weeks at 45° C. in an incubator. The oils were analyzed weekly during the storage period using the Racimat & Lovibond devices. The results obtained are as shown in Tables 5 and 6.

TABLE 5

| | Rancimat values | | |
|---|---|---|---|
| Storage time | Starting Material | High-grade Refined palm oil | Eluate |
| 1 week | 13.39 | 13.60 | 15.04 |
| 2 weeks | 13.32 | 12.63 | 14.31 |
| 3 weeks | 12.93 | 12.96 | 13.42 |
| 4 weeks | 13.20 | 12.50 | 12.68 |
| 5 weeks | 12.26 | 12.77 | 12.75 |
| 6 weeks | 12.15 | 11.77 | 12.51 |
| 7 weeks | 12.00 | 11.13 | 12.53 |
| 8 weeks | 11.59 | 11.36 | 11.75 |
| 9 week | 11.04 | 11.2 | 11.84 |

TABLE 6

| | Lovibond values | | |
|---|---|---|---|
| Storage time | Starting Material | High-grade Refined palm oil | Eluate |
| 2 weeks | 50Y 3.3R | 20Y 1.4R | 9Y 1.6R |
| 3 weeks | 50Y 3.3R | 20Y 1.4R | 9Y 1.6R |
| 4 weeks | 40Y 3.7R | 20Y 1.8R | 9Y 1.6R |
| 5 weeks | 40Y 3.7R | 20Y 2.0R | 9Y 1.6R |
| 6 weeks | 40Y 3.7R | 20Y 2.0R | 9Y 1.6R |
| 7 weeks | 40Y 3.7R | 20Y 2.0R | 9Y 1.6R |
| 8 weeks | 40Y 3.7R | 20Y 2.0R | 9Y 1.6R |
| 9 week | 40Y 3.9R | 20Y 2.0R | 9Y 1.6R |

The results in Tables 5 and 6 show that the storage stability of the triglyceride oil obtained by the process of the invention is better than the starting material (RBD palm oil) and the high-grade refined palm oil (JGQPO).

Example 4

Four different vegetable oils were subjected to size exclusion chromatography in the same way as the RBD palm oil in Example 2. The results so obtained are shown in Table 7.

TABLE 7

| | Canola (wt %) | | Sunflower (wt %) | | Soybean (wt %) | | Olive (wt %) | |
|---|---|---|---|---|---|---|---|---|
| | Before | After | Before | After | Before | After | Before | After |
| DG - C34 | 0 | 0 | 0 | 0 | 0 | 0 | 0 | 0 |
| DG - C36 | 0.11 | 0 | 0.18 | 0 | 0.13 | 0 | 0.4 | 0 |
| DG - C38 | 0.75 | 0.14 | 1.19 | 0.16 | 0.49 | 0 | 1.58 | 0 |
| TG - C46 | 0.27 | 0.3 | 0.12 | 0.13 | 0.09 | 0.09 | 0 | 0 |
| TG - C48 | 0 | 0 | 0 | 0 | 0 | 0 | 0.09 | 0 |
| TG - C50 | 1.21 | 1.3 | 1.32 | 1.35 | 3.21 | 3.22 | 4.07 | 3.77 |
| TG - C52 | 14.37 | 14.59 | 17.82 | 18.01 | 26.55 | 26.78 | 27.9 | 28.72 |
| TG - C54 | 78.37 | 78.88 | 76.96 | 78.17 | 67.57 | 68.1 | 64.19 | 65.94 |
| TG - C56 | 4.92 | 4.79 | 2.41 | 2.19 | 1.95 | 1.81 | 1.57 | 1.57 |

The results in Table 7 show that the process of the invention can also be applied to other oils and fats, not limited to palm oil.

The above is a description of the subject matter the inventor regards as the invention and is believed that others can and will design alternative systems that include this invention based on the above disclosure.

The invention claimed is:

1. A process for refining a glyceride oil to obtain a fraction enriched in triglyceride, the process comprising:
    passing a glyceride oil through a size exclusion column packed with porous particles having a mass weighted mean particle size of 20 gm to 1,000 gm and an average pore size of 10 Å to 150 Å to remove partial glyceride without using any solvent; and
    collecting an eluate fraction enriched in triglyceride;
    wherein the partial glyceride content of the triglyceride enriched fraction expressed in wt. % is at least 50% lower than the partial glyceride content of the glyceride oil; and
    wherein the glyceride oil that is used as the starting material in the process is selected from non-hydrogenated vegetable oil, a fraction of such an oil or a combination of two or more of these oils, and said vegetable oil being selected from palm oil, palm kernel oil, coconut oil, sunflower oil, soybean oil, rapeseed oil, linseed oil, olive oil and combinations thereof, and
    wherein the triglyceride enriched eluate fraction comprises at least 99 wt % of triglyceride and an amount of diglyceride, such amount of diglyceride being less than 0.3 wt % of diglyceride.

2. The process according to claim 1, wherein the glyceride oil contains 80 wt % to 99.8 wt % of triglyceride and 1 wt % to 20 wt % of partial glyceride.

3. The process according to claim 2, wherein the partial glyceride is selected from the group consisting of monoglyceride, diglyceride, glycerophospholipid and a combination thereof.

4. The process according to claim 1, wherein the glyceride oil contains 90 wt % to 99.8 wt % of triglyceride, 0.2 wt % to 7.0 wt % of diglycerides, 0 wt % to 3 wt % of monoglycerides and 0 wt % to 4 w % of glycerophospholipids.

5. The process according to claim 1, wherein the fraction enriched in triglyceride contains at least 98 wt % of triglyceride and less than 2 wt % of partial glyceride.

6. The process according to claim 1, further comprising:
    passing a solvent through the size exclusion column after the eluate fraction enriched in triglyceride is collected to obtain a solvent extract containing a partial glyceride enriched fraction; and
    isolating the partial glyceride enriched fraction from the solvent extract.

7. The process according to claim 6, wherein the partial glyceride enriched fraction is selected from the group consisting of monoglycerides, diglycerides, glycerophospholipids and a combination thereof.

8. The process according to claim 6, wherein the solvent is selected from the group consisting of acetone, C5-C8 alkanes and combinations thereof.

9. The process according to claim 1, wherein the glyceride oil contains phosphorous in an amount of not more than 10 mg/kg.

10. The process according to claim 1, wherein at least 80 wt % of the porous particles having a diameter in the range of 60 to 800 gm.

11. The process according to claim 1, wherein the porous particles having a surface area of 200 to 1200 m2/g.

12. The process according to claim 1, wherein the porous particles having pore size in the range of 35 to 90 Å.

13. The process according to claim 1, wherein the porous particles are selected from the group consisting of porous silica particles, porous cross-linked polystyrene particles and combination thereof.

14. The process according to claim 13, wherein the porous particles are porous silica particles.

15. A triglyceride oil that is obtained as the triglyceride enriched eluate fraction from a process comprising:
    passing a glyceride oil through a size exclusion column packed with porous particles having a mass weighted mean particle size of 20 lam to 1,000 lam and an average pore size of 10 A to 150 A to remove partial glyceride without using any solvent; and
    collecting an eluate fraction enriched in triglyceride,
    wherein the partial glyceride content of the triglyceride enriched eluate fraction expressed in wt. % is at least 50% lower than the partial glyceride content of the glyceride oil, and
    wherein the glyceride oil that is used as the starting material in the process is selected from non-hydrogenated vegetable oil, a fraction of such an oil or a combination of two or more of these oils, and said vegetable oil being selected from palm oil, palm kernel oil, coconut oil, sunflower oil, soybean oil, rapeseed oil, linseed oil, olive oil and combinations thereof, and
    wherein the triglyceride enriched eluate fraction comprises at least 99 wt % of triglyceride and an amount of diglyceride, such amount of diglyceride being less than 0.3 wt % of diglyceride.

16. The triglyceride oil according to claim 15, wherein the triglyceride oil contains at least 99.9 wt % of triglyceride and less than 0.1 wt % of diglyceride.

* * * * *